United States Patent
Weinstein

(10) Patent No.: US 7,534,804 B2
(45) Date of Patent: May 19, 2009

(54) BENZOXAZOLE INHIBITORS OF 15-LIPOXYGENASE

(75) Inventor: David S. Weinstein, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 435 days.

(21) Appl. No.: 11/509,373

(22) Filed: Aug. 24, 2006

(65) Prior Publication Data

US 2007/0049628 A1 Mar. 1, 2007

Related U.S. Application Data

(60) Provisional application No. 60/711,070, filed on Aug. 24, 2005, provisional application No. 60/713,493, filed on Sep. 1, 2005.

(51) Int. Cl.
*A61K 31/423* (2006.01)
*C07D 263/54* (2006.01)

(52) U.S. Cl. ............... 514/375; 548/215; 548/217; 514/374

(58) Field of Classification Search ......... 548/215, 548/217; 514/374, 375
See application file for complete search history.

(56) References Cited

U.S. PATENT DOCUMENTS

| | | | |
|---|---|---|---|
| 5,612,359 A | 3/1997 | Murugesan | |
| 5,712,279 A | 1/1998 | Biller et al. | |
| 5,739,135 A | 4/1998 | Biller et al. | |
| 5,760,246 A | 6/1998 | Biller et al. | |
| 6,043,265 A | 3/2000 | Murugesan et al. | |
| 6,548,529 B1 | 4/2003 | Robl et al. | |
| 6,576,630 B1 * | 6/2003 | Link et al. | 514/233.8 |
| 6,706,720 B2 | 3/2004 | Atwal et al. | |

FOREIGN PATENT DOCUMENTS

WO WO00/01389 1/2000

OTHER PUBLICATIONS

Bleich. D. et al., "Resistance to type 1 diabetes induction in 12-lipoxygenase knockout mice", The J. of Clinical Investigation, vol. 103(10), pp. 1431-1436 (1999).
Bocan, T. et al., "A specific 15-lipoxygenase inhibitor limits the progression and monocyte-macrophage enrichment of hypercholesterolemia-induced atherosclerosis in the rabbit", Atherosclerosis, vol. 136, pp. 203-216 (1998).
Gan, Q. et al., "Defining the Arachidonic Acid Binding site of human 15-Lipoxygenase", The J. of Biological Chemistry, vol. 271(41), pp. 25412-25418 (1996).
Jiang, Z. et al., "Lipid Hydroperoxide Measurement by Oxidation of $Fe^{2+}$ in the Presence of Xylenol Orange. Comparison with the TBA Assay and an Iodometric Method", Lipids, vol. 26(10), pp. 853-856 (1991).
Kelavkar, U. et al., "The Effect of 15-Lipoxygenase-1 Expression on Cancer Cells", Current Urology Reports, vol. 3, pp. 207-214 (2002).
Rapoport, S. et al., "The Lipoxygenase of Reticulocytes. Purification, Characterization and Biological Dynamics of the Lipoxygenase: Its Identity with the Respiratory Inhibitors of the Reticulocyte", Eur. J. Biochem., vol. 96, pp. 545-561 (1979).
Setty, B. et al., "15-Hydroxyeicosatetraenoic Acid-Mediated Potentiation of Thrombin-Induced Platelet Functions Occures Via Enhanced Production of Phosphoinositide-Derived Second Messengers-sn-1,2-Diacylglycerol and Inositol-1,4,5-Trisphosphate", Blood, vol. 80(11), pp. 2765-2773 (1992).
Sultana, C. et al., "Lipoxygenase Metabolites induced expression of Adhesion Molecules and Transendothelial Migration of Monocyte-Like HL-60 Cells is Linked to Protein Kinase C Activation", J. of Cellular Physiology, vol. 167, pp. 477-487 (1996).
Tisdale, M., "Protein Loss in Cancer Cachexia", Science, vol. 289, pp. 2293-2294 (2000).

* cited by examiner

*Primary Examiner*—Golam M Shameem
(74) *Attorney, Agent, or Firm*—Hong Liu

(57) ABSTRACT

The present application provides benzoxazole inhibitors of 15-LO, pharmaceutical compositions containing such inhibitors and methods for treating diseases related to the 15-LO cascade using such compounds and compositions.

8 Claims, No Drawings

BENZOXAZOLE INHIBITORS OF 15-LIPOXYGENASE

RELATED APPLICATIONS

This application claims priority benefit under Title 35 § 119(e) of U.S. Provisional Application No. 60/711,070, filed Aug. 24, 2005, and U.S. Provisional Application No. 60/713,493, filed Sep. 1, 2005, the contents of which are herein incorporated by reference.

BACKGROUND OF THE INVENTION

The 15-LO cascade is implicated in various inflammatory disorders, including disorders involving the origin and recruitment of foam cells. Cholesterol is transported in blood particles called lipoproteins, which include low-density lipoproteins (LDL). Lipoproteins contain cholesterol and are necessary for foam cell formation. The formation of foam cells can lead to serious disorders. For example, hypercholesterolemia can induce monocytes to migrate into the arterial wall and mature into foam cells or tissue macrophages that accumulate fatty material, including cholesterol esters. Continued creation of foam cells thickens the inner lining of medium and large arteries, thereby forming atherosclerotic plaques or lesions containing cholesterol, smooth muscle cells, and connective tissue cells. Affected arteries lose elasticity and become narrowed or obstructed by the plaques indicating the onset of atherosclerosis. Atherosclerotic plaques may collect calcium, become brittle, and even rupture triggering the formation of a blood clot or thrombus capable of occluding an artery and causing a stroke or heart attack. In addition to atherosclerosis, hypercholesteremia plays a role in peripheral vascular diseases of small arteries, veins and lymphatics. Thus, hypercholesteremia may also affect the arms, legs, kidneys and other vital organs in addition to the heart and brain.

Lipoxygenases are enzymes that catalyze the oxidation of polyunsaturated fatty acids and esters thereof, including those found in low-density lipoproteins. In addition to metabolism of free fatty acids, the enzyme 15-lipoxygenase (15-LO) also oxidizes esterified polyenoic fatty acids. Related to its general pathology, it is believed that oxidative metabolites of the 15-LO cascade [e.g. the arachidonic acid metabolite 15-hydroperoxyeicosatetraenoic acid (15-HPETE)], induce endothelial cell activation and subsequent adhesion molecule expression resulting in monocyte recruitment to the vessel wall [Sultana et al, J. of Cellular Physiology 167 (1996) 467-487]. 15-Hydroxyeicosatetraenoic acid (15-HETE), a reduction product of 15-HPETE, has also been implicated in the potentiation of thrombin-induced platelet activation [Setty et al, Blood, 80:11 (1992): 2765-2773]. It has also been demonstrated that arachidonic acid metabolites of the 15-LO cascade, namely 15-hydroperoxyeicosatetraenoic acid (15-HPETE), induce a pro-thrombotic state in endothelial cells through enhancement of plasminogen activator inhibitor-1 (PAI-1) release. Additionally, evidence that 15-LO is involved in the pathology of diabetes, it has been demonstrated that deletion of the mouse gene homologue of 15-LO leads to a reduction of disease progression [Bleich et al, *J Clin Invest* (1999) May 15;103(10):1431-6]. 15-LO has also been implicated in the progression of various cancers [Kelavkar et al, *Curr Urol Rep* 2002 June;3(3):207-14]. Not only in the progression of the cancer itself, but also in its related pathologies including cachexia and wasting [Tisdale et al, *Science* 2000 Sep. 29;289(5488):2293-4].

Inhibition of 15-LO, therefore, would be useful to prevent and treat diseases with either an inflammatory component, a thrombotic component, or both as in the case of atherosclerosis, as well as various cancers. For example, it has been shown that treatment with a 15-LO inhibitor suppressed atherogenesis (or the production of atheroma—a fatty degeneration of the arterial wall) in rabbits fed a high-fat diet [Bocan et al, *Atherosclerosis*, 136 (1998): 203-216]. Additional diseases in which treatment with a 15-LO inhibitor would be useful include asthma, psoriasis, osteoarthritis, rheumatoid arthritis, Alzheimer's disease, and chronic obstructive pulmonary disease.

DETAILED DESCRIPTION OF THE INVENTION

The present application provides benzoxazole inhibitors of 15-LO, pharmaceutical compositions containing such inhibitors, and methods for treating diseases related to the 15-LO cascade using such compounds and compositions. Specifically, the application provides compounds of Formula I:

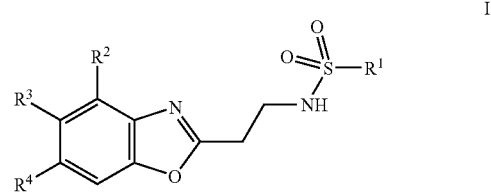

including all stereoisomers, pharmaceutically acceptable salts, prodrugs and solvates thereof wherein, n, $R^1$, X, Y and Z are defined herein.

DEFINITIONS

The following are definitions of terms used in this specification. The initial definition provided for a group or term herein applies to that group or term throughout the present specification, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are often most preferred.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like.

The term "perfluoroalkyl" as used herein by itself or as part of another group refers to an alkyl group wherein the hydrogen atoms have been replaced by fluorine atoms.

The term "alkoxy" as used herein by itself or as part of another group refers to an alkyl, alkenyl or alkynyl group attached as a substituent through an ether, —O—, linkage.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

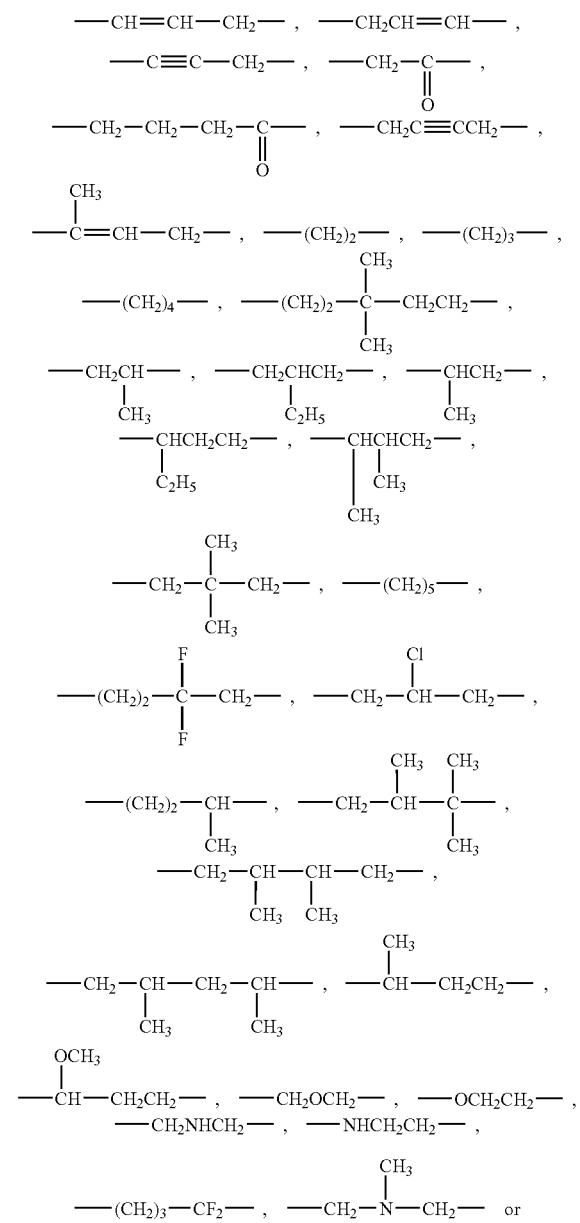

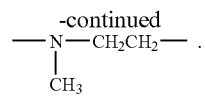

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

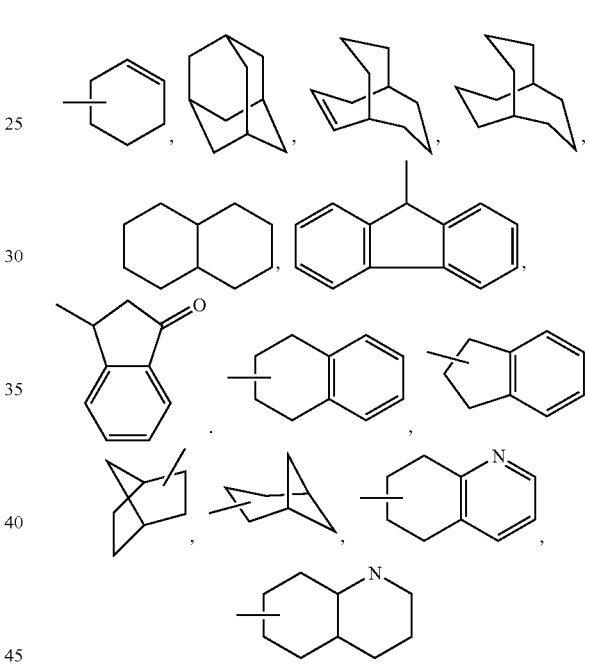

and the like.

The term "cycloalkylene" as employed herein refers to a "cycloalkyl" group which includes free bonds and thus is a linking group such as

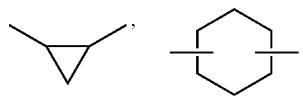

and the like.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

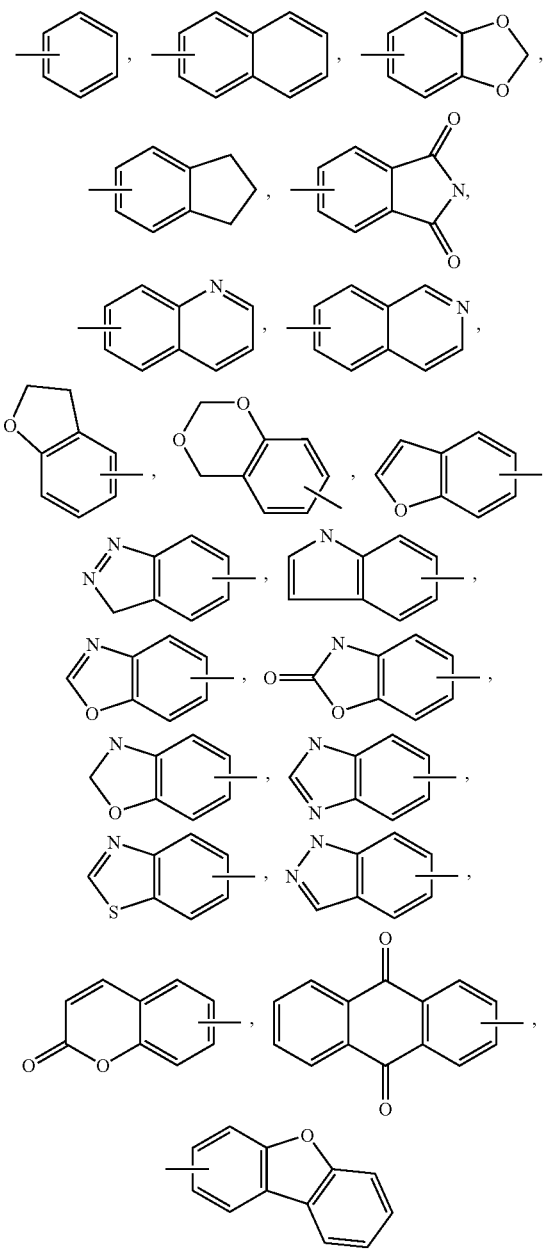

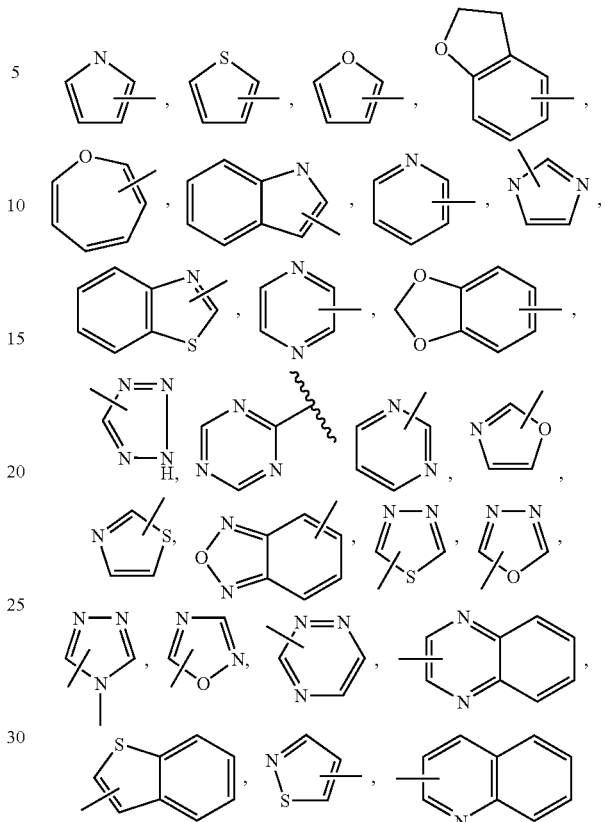

and the like.

The terms "halogen" and "halo" as used herein by itself or as part of another group refer to fluorine, chlorine, bromine and iodine. Haloalkyl refers to an alkyl chain substituted with from one to three halogens.

The term "heteroaryl" as used herein by itself or as part of another group refers to monocyclic, bicyclic and tricyclic aromatic rings containing from 5 to 113 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include the following:

and the like.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

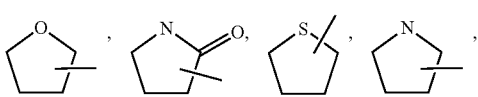

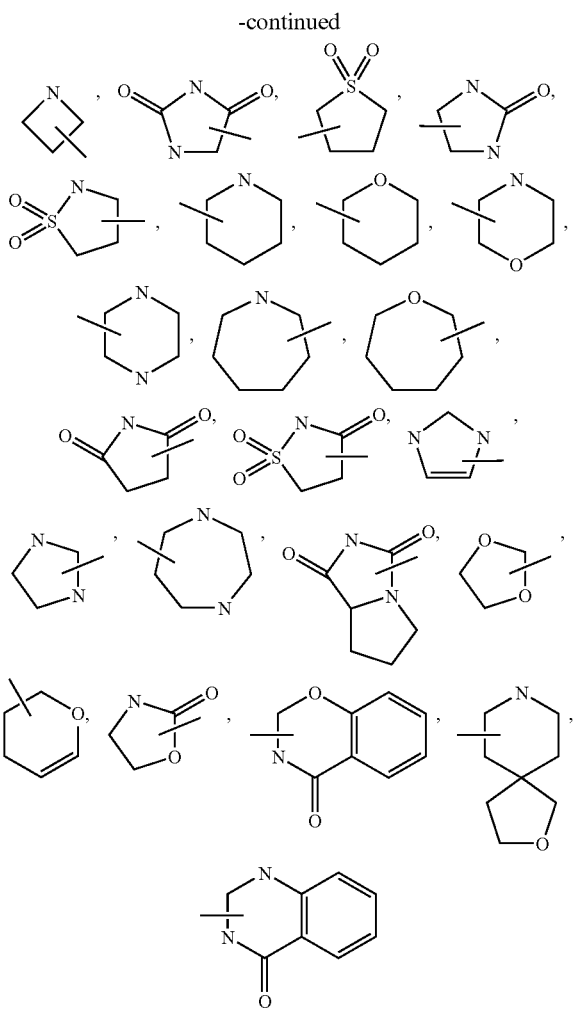

and the like.

The term "carboxylic acid" as used herein by itself or as part of another group refers to the group —C(O)OH.

The term "ester" as used herein by itself or as part of another group refers to the groups —C(O)O— and —O(O)C—, wherein the groups are further substituted with groups such as, for example, alkyl, alkenyl, alkynyl, perfluoroalyl, cycloalkyl, heterocyclic, aryl, heteroaryl.

The term "amide" as used herein by itself or as part of another group refers to the groups

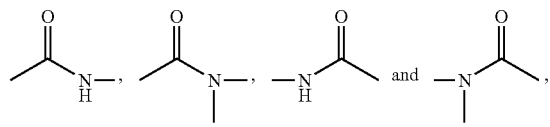

wherein the groups are further substituted with groups such as, for example, alkyl, alkenyl, alkynyl, perfluoroalyl, cycloalkyl, heterocyclic, aryl, heteroaryl.

The term "amine" as used herein by itself or as part of another group refers to the groups

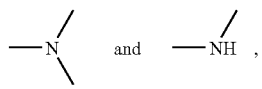

wherein the groups are further substituted with groups such as, for example, alkyl, alkenyl, alkynyl, perfluoroalyl, cycloalkyl, heterocyclic, aryl, heteroaryl.

The above-defined groups may optionally have one or more hydrogen atoms that are attached to a carbon atom substituted with any group known to one of skill in the art.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl), and each of which (homocyclic or heterocyclic) may optionally be substituted by one or more (such as one to three) hydrogen, halogen, cyano, alkyl, alkoxy, nitro or trifluoromethyl groups.

Throughout the specification, groups and substituents thereof may be chosen to provide stable moieties and compounds.

The compounds of formula I form salts which are also within the scope of this application. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the application are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present application.

All stereoisomers of the present compounds, such as those which may exist due to asymmetric carbons on the R substituents, including enantiomeric forms (which may exist even in the absence of asymmetric carbons, e.g., atropisomers) and diastereomeric forms, are contemplated within the scope of this application. Individual stereoisomers of the compounds of the application may, for example, be substantially free of other isomers, or may be admixed, for example, as racemates or with all other, or other selected, stereoisomers. The chiral centers of the present application can have the S or R configuration as defined by the IUPAC 1974 Recommendations.

Methods of Preparation

The compounds of the present application may be synthesized by many methods available to those skilled in the art of organic chemistry. General synthetic schemes for preparing compounds of the present application are described below. These schemes are illustrative and are not meant to limit the possible techniques one skilled in the art may use to prepare the compounds disclosed herein. Different methods to prepare the compounds of the present application will be evident to those skilled in the art. Additionally, the various steps in the synthesis may be performed in an alternate sequence in order to give the desired compound or compounds. Examples of compounds of the present application prepared by methods described in the general schemes are given in the preparations and examples section set out hereinafter.

The benzoxazoles of the present application may be prepared by the condensation of ortho-amino phenols with imidates (iminoethers) as shown in Scheme 1. Thus, treatment of 3-amino propionitrile with an appropriate sulfonylating reagent, such as a sulfonyl chloride ($R^1SO_2Cl$) in the presence of a tertiary amine base (triethylamine, N,N-diisopropylethylamine, or the like) provides an intermediate sulfonamide I. The cyano functionality may be converted to an imidate ester by the well-known Pinner reaction. Thus, treatment of I with a strong mineral acid (typically gaseous hydrochloric acid) in an alcohol (methanol or ethanol) solvent provides the intermediate imidate II which may be isolated as a salt by simply removing the volatiles under reduced pressure. Condensation of the imidate (or salt thereof) with a suitably functionalized o-aminophenol III may be effected by refluxing a mixture of the two in ethanol or methanol to give the benzoxazole IV. In preparing benzoxazoles with carboxamide groups at C-5 of the benzoxazole ($R^3=CONHR^{10}$), the imidate II may be condensed with an o-aminophenol bearing a carboxylic acid group at C-4 (III, $R^3=CO_2H$). An amide (V) may then be prepared by condensation of the benzoxazole carboxylic acid (IV, $R^3=CO_2H$) with an appropriate amine ($R^{10}NH_2$) and a suitable carboxylic acid activating reagent. For example, the acid is may be activated with 1-hydroxy-7-azabenzotriazole (HOAt) in the presence of a carbodiimide (typically 1-(3-dimethylaminopropyl)-3-ethylcarbodiimide hydrochloride, EDC).

Alternatively, benzoxazoles may be prepared by a sequence of acylation of a 2-aminophenol followed by cyclodehydration (Scheme II). For examples of the present application, the acylating partner VI may be prepared by hydrolysis of the nitrile I under the usual conditions for alkyl nitrile hydrolysis (9N sulfuric acid, or aqueous sodium hydroxide/ hydrogen peroxide, or aqueous sodium peroxide). Condensation of the carboxylic acid VI with o-aminophenols (III) was found to proceed smoothly by pre-activation of the acid alone with 1,1-carbonyldiimidazole (CDI) followed by condensation of the acid imidazolide (typically not isolated) with o-aminophenol III to give amide phenol VII. Cyclodehdration of VII may be effected under standard dehydrative conditions (typically, heating in glacial acetic acid) to give benzoxazole IV. In cases where IV is a carboxylic acid ($R^3$ or $R^4=CO_2H$), amide derivatives (V and VII, respectively) may be prepared following the procedure described above for the preparation of amide V.

Scheme 1
Preparation of benzoxazoles via intermediate imidate esters

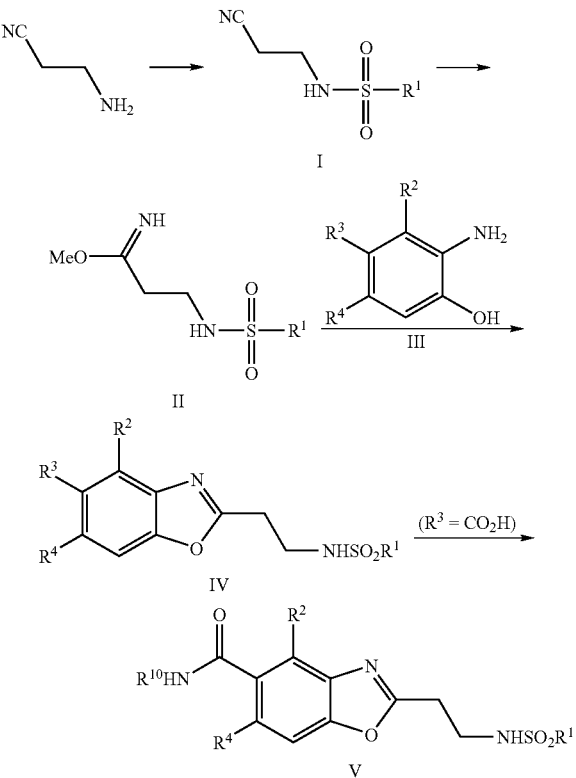

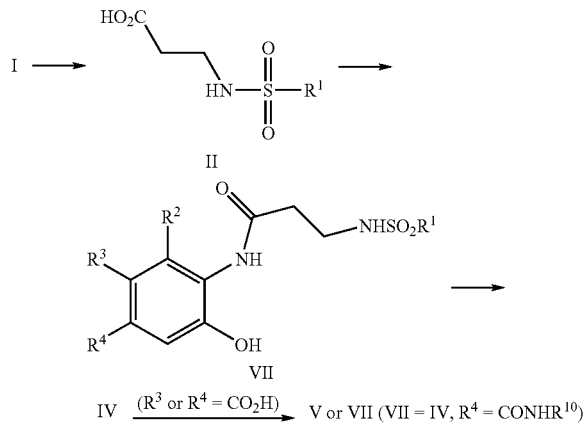

Scheme 2
Preparation of benzoxazoles via acylation/cyclodehydration sequence

Utility and Combinations

The compounds of formula I and salts thereof are inhibitors of 15-LO and are useful in treatment of various inflammatory disorders, including disorders involving the origin and recruitment of foam cells. The compounds of the present application may be employed alone or in combination with each other and/or other suitable therapeutic agents useful in the treatment of 15-LO mediated disorders such as atherosclerosis, treating or preventing inflammation; diabetes; vascular restenosis; hypertension; asthma; rheumatiod arthritis; osteoarthritis; cancer; and inflammatory bowel disease.

Additionally, the compounds are useful in treating or preventing symptoms or consequences occurring from thrombosis and/or the formation of atherosclerotic plaques, atherosclerosis, peripheral arterial disease, coagulation syndromes, and intermittent claudication. The compounds may be used to treat thrombotic or thromboembolic conditions such as thromboembolic stroke (including that resulting from atrial fibrillation or from ventricular mural thrombus); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, hormome replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequenses of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation); coagulation syndromes; vascular remodeling atherosclerosis, restenosis and systemic infection; prevention of metastesis and tumor implantation; diabetic complications including retinopathy, nephropathy and neuropathy; inflammation; Kasabach-Merritt syndrome; atrial fibrillation; ventricular enlargement (including dilated cardiac myopathy and heart failure); restenosis (e.g., following arterial injury-induced either endogenously or exogenously).

In addition, the compounds of the present application may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present application may be useful for maintaining blood vessel patency in conjunction with interventional cardiology or vascular surgery including bypass grafting, arterial reconstruction, atherectomy, vascular graft and stent patency, organ, tissue and cell implantation and transplantation. Additionally, the compounds may be used for preservation of tissue as related to organ transplantation.

The inventive compounds also are useful in treating diseases or disorders in other tissues or muscles that are associated with inflammatory conditions. For example, the compounds may be used to treat muscle cell damage and necrosis.

Additionally, the inventive compounds may be useful as anti-cancer and/or anti-tumor agents.

The present application thus provides methods for the treatment of these disorders, comprising the step of administering to a subject in need thereof at least one compound of the formula I in an amount effective therefor. Other therapeutic agents such as those described below may be employed with the inventive compounds in the present methods. In the methods of the present application, such other therapeutic agent(s) may be administered prior to, simultaneously with or following the administration of the compound(s) of the present application.

The effective amount of a compound of the present application may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent or angiotensin II-dependent disorders.

The present application also provides pharmaceutical compositions comprising at least one of the compounds of the formula I capable of treating a 15-LO mediated disorder in an amount effective therefor, and a pharmaceutically acceptable vehicle, carrier or diluent. The compositions of the present application may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used.

Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the application may be administered topically to treat peripheral vascular diseases and as such may be formulated as a cream or ointment.

The compounds of the present application may also be employed in combination with other suitable therapeutic agents that a patient suffering from a 15-LO mediated disorder might also likely be taking other therapeutic agents such as potassium channel openers, calcium channel blockers, sodium hydrogen exchanger inhibitors, anti-arrhythmic agents, thrombin inhibitors, platelet aggregation inhibitors or anti-platelet agents, fibrinogen antagonists, diuretics, anti-hypertensive agents, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-oxidant agents; angiogenesis modulators; anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

For example, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include:

anti-arrhythmic agents including Class I agents (such as propafenone); Class II agents (such as carvedilol and propranolol); Class III agents (such as sotalol, dofetilide, amiodarone, azimilide and ibutilide); Class IV agents (such as ditiazem and verapamil); K+ channel openers such as IAch inhibitors, and IKur inhibitors (e.g., compounds such as those disclosed in U.S. application Ser. No. 09/729,731, filed Dec. 5, 2000;

alpha- or beta- adrenergic blockers (such as propranolol, nadolol and carvedilol), or β-adrenergic agonists such as albuterol, terbutaline, formoterol, salmeterol, bitolterol, pilbuterol, and/or fenoterol;

angiotensin-II receptor antagonists (e.g., irbesartan, losartan or valsartan);

anticholinergics such as ipratropium bromide;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-depressant or anti-anxiety agents such as nefazodone, sertraline, diazepam, lorazepam, buspirone, and hydroxyzine pamoate;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-hypertensive agents such as angiotensin-converting enzyme (ACE) inhibitors (e.g., captopril, lisinopril, zofenopril, ramipril, fosinopril, enalapril, ceranopril, cilazopril, delapril, pentopril, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors;

anti-inflammatory agents such as cromolyn, nedocromil, theophylline, zileuton, zafirlukast, monteleukast and/or pranleukast or cortiocosteroids including beclomethasone, triamcinolone, budesonide, fluticasone, flunisolide or dexamethasone; prednisone; dexamethasone; enbrel; protien tyrosine kinase (PTK) inhibitors; cyclooxygenase inhibitors (including NSAIDs, and COX-1 and/or COX-2 inhibitors); aspirin; or indomethacin; other lipoxygenase inhibitors; chemokine receptor modulators (including CCR1, CCR2, CCR3, CXCR2 receptor antagonists); secretory and cytosolic phospholipase A2 inhibitors; VLA4 antagonists; cytokine modulators (e.g. TNF-alpha converting enzyme (TACE) inhibitors, Interleukin-1 converting enzyme (ICE) inhibitors, Interleukin-1 receptor antagonists);

angiogenesis modulators such as endostatin;

anti-oxidant agents and/or lipid peroxidation inhibitors such as probucol, BO-653, Vitamin A, Vitamin E, AGI-1067;

anti-platelet agents such as GPIIb/GPIIIa blockers, (e.g., abciximab, eptifibatide, tirofiban); P2Y12 antagonists (e.g., clopidogrel, ticlopidine, CS-747); or thromboxane receptor antagonists (e.g., ifetroban);

anti-osteoporosis agents including alendronate and raloxifene;

anti-obesity agents including orlistat and aP2 inhibitors (such as those disclosed in U.S. Ser. No. 09/519,079 filed Mar. 6, 2000);

anti-proliferative agents for use in combination with the compounds of the present application include cyclosporin A, paclitaxel, FK 506, and adriamycin;

anti-ulcer and gastroesophageal reflux disease agents including famotidine, ranitidine, and omeprazole;

sodium hydrogen exchanger-1 (NHE-1) inhibitors such as cariporide;

calcium channel blocking agents such as verapamil, nifedipine, diltiazem, amlodipine and mybefradil;

cardiac glycosides such as digitalis and ouabain;

diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride;

hormone replacement therapies including estrogen (e.g., congugated estrogens) and estradiol;

lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, or atavastatin or visastatin)); squalene synthetase inhibitors; fibrates; bile acid sequestrants (such as questran); ACAT1 inhibitors; ACAT2 inhibitors; dual ACAT½ inhibitors; MTP inhibitors; cholesterol absorption inhibitors such as Eztemibe; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists;

mineralocorticoid receptor antagonists such as spironolactone and eplirinone;

microsomal triglyceride transport protein inhibitors (such as disclosed in U.S. Pat. Nos. 5,739,135, 5,712,279 and 5,760,246);

phosphodiesterase (PDE) inhibitors including dipyridamole, cilostazol, or sildenafil, or PDE inhibitors in combination with aspirin, ifetroban, picotamide, ketanserin, clopidogrel, and/or thromboxane receptor antagonists or thromboxane A synthetase inhibitors (such as picotamide);

serotonin-2-receptor antagonists (such as ketanserin), fibrinogen receptor antagonists, and thrombolytic agents, such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), factor VIIa inhibitors, factor Xa inhibitors, thrombin inhibitors (such as hirudin and argatroban), animal salivary gland plasminogen activators, PAI-1 inhibitors such as XR-330 and T-686, and inhibitors of $\alpha$-2-antiplasmin such as anti-$\alpha$-2-antiplasmin antibody, prostacyclin mimetics.

The inventive compounds may also be useful in combination with other anticancer strategies and chemotherapies such as taxol and/or cisplatin. The compounds may be used in conjunction with anti-tumor agents such as paclitaxel, adriamycin, epithilones, cisplatin, and carboplatin.

The various other therapeutic agents described above may be employed in the same dosage form with the compound of formula I or in different dosage forms, in dosages and regimens as generally known in the art or in the PDR.

The compounds of the present application may act in a synergistic fashion with one or more of the above agents to allow for increased efficacy and/or reduced doses of any of the above agents and therefore minimize potential hemorrhagic side-effects.

If formulated as a fixed dose, such combination products employ the compounds of this application within the dosage range described and the other pharmaceutically active agent within its effective dosage range. The above other therapeutic agents, when employed in combination with the compounds of the present application, may be used, for example, in those amounts indicated in the Physicians' Desk Reference (PDR) or as otherwise determined by one of ordinary skill in the art.

The following assays may be employed in ascertaining the degree of activity of a compound as a 15-LO inhibitor. Compounds described in the following Examples have demonstrated measurable activity as 15-LO inhibitors. The inhibitory activity of the Examples against purified 15-LO enzyme was determined using a standard calorimetric assay in which the lipid hydroperoxide product of either linoleic or arachidonic acid [13-hydroperoxyoctadecadienoic acid (13-HPODE) and 15-hydroperoxyeicosatetraenoic acid (15-HPETE), respectively] oxidizes $Fe^{2+}$ under mildly acidic conditions [Jiang et al, Lipids (1991), 26:10, 853-856]. The $Fe^{3+}$ forms a chromophore with xylenol orange that absorbs strongly at 560 nm. Inhibitory activity was compared to an uninhibited (maximal) reaction to yield % inhibition (compound concentration in which enzyme activity is reduced by 50% is termed the IC50). 15-LO enzyme was obtained from phenylhydrazine-treated rabbits and purified according to the method of Rapoport et al [European Journal of Biochemistry (1979) 96:545-561]. In addition to the colorimetric assay, a standard spectrophotometric kinetic assay [Gan et al, J. Biological Chemistry (1996), 271:41; 25412-2541877] was also employed to measure compound activity as 15-LO inhibitors. This assay determines enzyme activity by monitoring the increased absorbance at 234 nm that results from conjugated diene formation of the metabolized substrate. Reactions were carried out 3 minutes and the linear part of the curve was utilized to calculate reaction rates. IC50 calculations were as described for the calorimetric assay.

EXAMPLES

The following Examples illustrate embodiments of the present application, and are not intended to limit the scope of the claims.

General Procedure:

Purification by Reverse-Phase Preparative HPLC

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol/water mixtures in the presence of 0.1% trifluoroacetic acid ("TFA").

Analytical HPLC Methods Employed in Characterization of Examples

Analytical HPLC was performed on Shimadzu LC10AS liquid chromatographs using of the following method:
Linear gradient of 0 to 100% solvent B over 4 minutes ("min"), with 1 min hold at 100% B.
Ultraviolet ("UV") visualization at 220 nanometers ("nm")
Column: YMC S5 ODS Ballistic 4.6×50 mm
Flow rate: 4 milliliters ("ml")/min
Solvent A: 0.2% phosphoric acid, 90% water, 10% methanol ("MeOH")
Solvent B: 0.2% phosphoric acid, 90% methanol, 10% water Example 1

N-(2-Benzooxazol-2-yl-ethyl)-4-pentyl-benzenesulfonamide

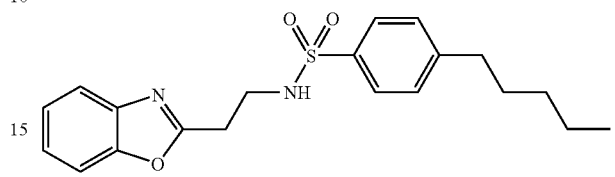

Step 1:
N-(2-Cyano-ethyl)-4-pentyl-benzenesulfonamide

To a solution of 3-aminoproprionitrile (0.57 g, 8.1 mmol) in dichloromethane (20 mL) at 0° C. was added triethylamine (1.69 mL, 12.2 mmol) followed by 4-N-pentylbenzenesulphonyl chloride (2.0g, 8.1 mmol). After 1 h at ambient temperature, the reaction mixture was diluted with ethyl acetate (100 mL) and washed with 1 N aqueous HCl. The organic layer was washed with saturated aqueous sodium bicarbonate followed by brine, dried over sodium sulfate and concentrated. The residue was purified by flash column chromatography (35% EtOAc/Hexanes) to give 1A as an oil which solidified upon standing.

Step 2:
3-(4-Pentyl-benzenesulfonylamino)-propionimidic acid ethyl ester hydrochloride Through a solution of 1A (700 mg, 2.5 mmol) in absolute ethanol (7 mL) at 0° C. was bubbled HCl gas for 15 min. The solution was warmed to ambient temperature. The solvent was removed in vacuo to give a sticky residue which dried on the pump to give 1B as a white powder.

Step 3: N-(2-Benzooxazol-2-yl-ethyl)-4-pentyl-benzenesulfonamide

A mixture of 1B (60 mg, 0.16 mmol) and 2-aminophenol (20 mg, 0.18 mmol) in ethanol (1.5 mL) was refluxed 75 min. The solvent was removed and the residue purified by flash column chromatography (30% EtOAc/Hexanes) to give the title compound as an oil which solidified upon standing. MS m/e 373; HPLC retention time 3.76 min.
$^1$H NMR (400 MHz, $CDCl_3$): 0.82 (t, 3H), 1.28 (m, 4H), 1.46 (dd, 2H), 2.55 (dd, 2H), 3.03 (dd, 2H), 3.45 (dd, 2 H), 7.20 (d, 2H), 7.26 (m, 2H), 7.39 (m, 1H), 7.57 (m, 1H), 7.70 (d, 2H)

Examples 2 to 10

The following examples 2 to 10 were prepared by the method described above for the preparation of the title compound of Example 1. Commercially available sulfonyl chlorides were substituted for 4-N-pentylbenzenesulphonyl chloride in Step 1, where appropriate. Likewise, commercially available substituted o-aminophenols were utilized in Step 3. HLPC retention times were determined using HPLC Method described in the General Method.

| Example # | Structure | Name | Rt (min) | M + H |
|---|---|---|---|---|
| 2 | 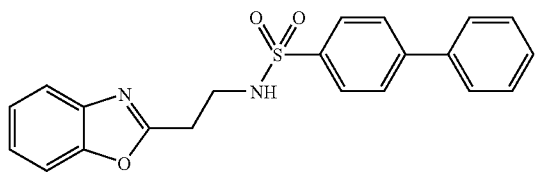 | Biphenyl-4-sulfonic acid (2-benzooxazol-2-yl-ethyl)-amide | 3.40 | 379 |
| 3 | 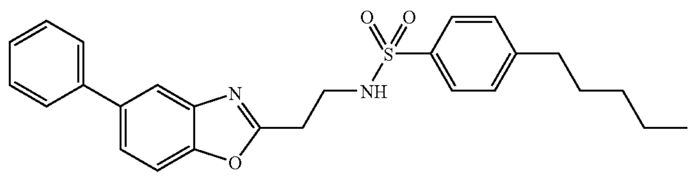 | Pentyl-N-[2-{5-phenyl-benzooxazol-2-yl)-ethyl]-benzenesulfonamide | 4.14 | 449 |
| 4 | 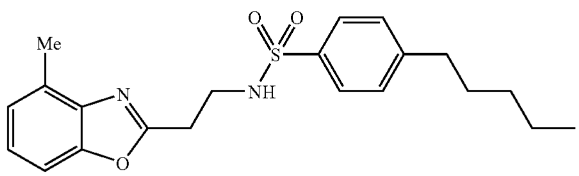 | N-[2-(4-Methyl-benzooxazol-2-yl)-ethyl]-4-pentyl-benzenesulfonamide | 3.92 | 387 |
| 5 | 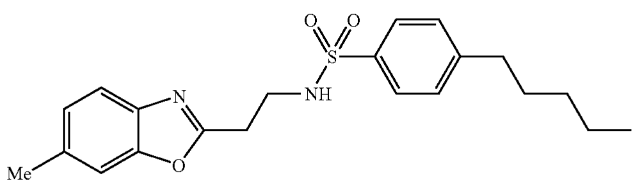 | N-[2-(6-Methyl-benzooxazol-2-yl)-ethyl]-4-pentyl-benzenesulfonamide | 3.92 | 387 |
| 6 | 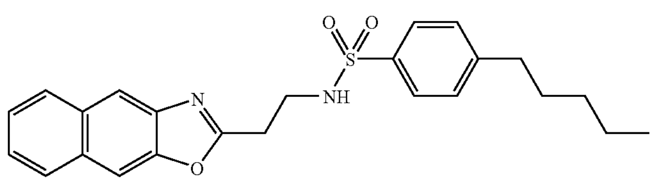 | N-(2-Naphtho[2,3-d]oxazol-2-yl-ethyl)-4-pentyl-benzenesulfonamide | 4.03 | 423 |
| 7 | 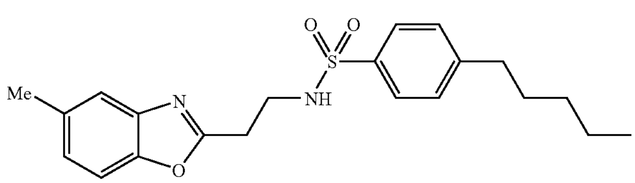 | N-[2-(5-Methyl-benzooxazol-2-yl)-ethyl]-4-pentyl-benzenesulfonamide | 3.90 | 449 |
| 8 | 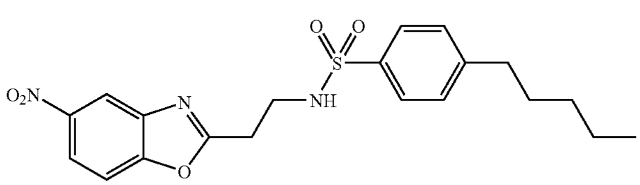 | N-[2-(5-Nitro-benzooxazol-2-yl)-ethyl]-4-pentyl-benzenesulfonamide | 3.72 | 418 |
| 9 | 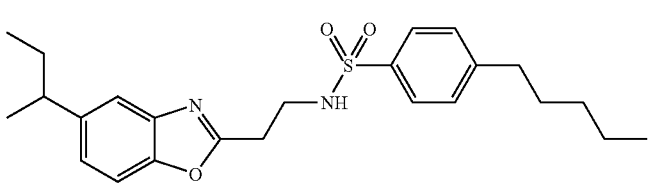 | N-[2-(5-sec-Butyl-benzooxazol-2-yl)-ethyl]-4-pentyl-benzenesulfonamide | 4.25 | 429 |

| Example # | Structure | Name | Rt (min) | M + H |
|---|---|---|---|---|
| 10 | 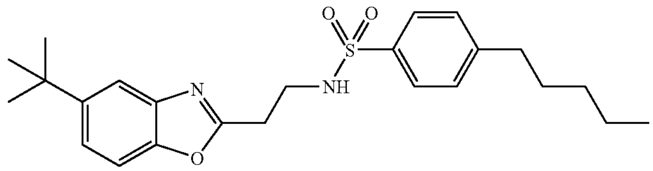 | N-(2-(5-tert-butylbenzo[d]oxazol-2-yl)ethyl)-4-pentylbenzenesulfonamide | 4.22 | 429 |

Example 11

N-(3-isopropylphenyl)-2-(2-(4-pentylphenylsulfonamido)ethyl)benzo[d]oxazole-5-carboxamide

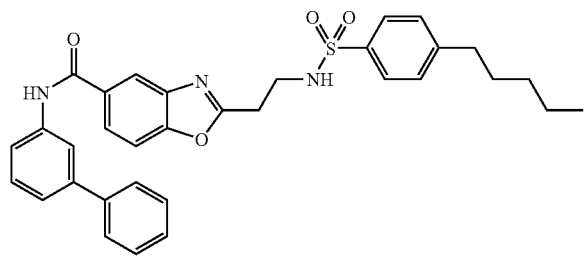

Step 1: 2-(2-(4-pentylphenylsulfonamido)ethyl)benzo[d]oxazole-5-carboxylic acid The title compound of Step 1 was prepared following the procedure described above for the preparation of the product of Step 3 of Example 1, substituting 3-amino-4-hydroxybenzoic acid in place of o-aminophenol. MS m/e 417; HPLC retention time 3.50 min.

Step 2:

To a solution of the product of Step 1 (32 mg, 0.076 mmol) in a mixture of acetonitrile (0.2 mL) and DMF (0.1 mL) were successively added HOAt (11 mg, 0.083 mmol), EDC (16 mg, 0.083 mmol), and 3-phenyl aniline (14 mg, 0.083 mmol). The mixture was heated at 50° C. for 1.5 h, then purified by preparative HPLC to give the product (15 mg, 37% yield) as a white solid. MS m/e 568; HPLC retention time 4.13 min.

Examples 12 to 18

The following examples 12 to 18 were prepared in a similar manner as the title compound of Example 11.

| Example # | Structure | Name | Rt (min) | M + H |
|---|---|---|---|---|
| 12 | 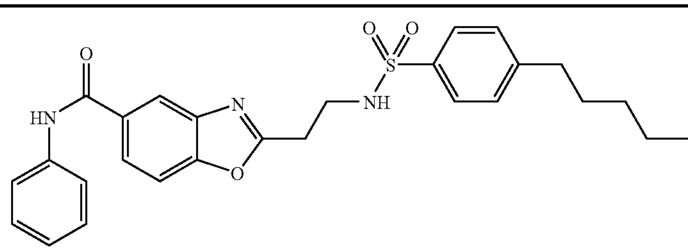 | 2-(2-(4-pentylphenylsulfonamido)ethyl)-N-phenylbenzo[d]oxazole-5-carboxamide | 3.82 | 492 |
| 13 | 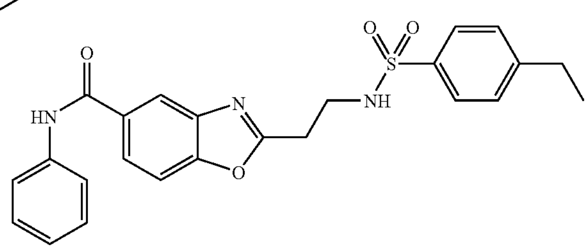 | 2-(2-(4-ethylphenylsulfonamido)ethyl)-N-phenylbenzo[d]oxazole-5-carboxamide | 3.26 | 450 |
| 14 | 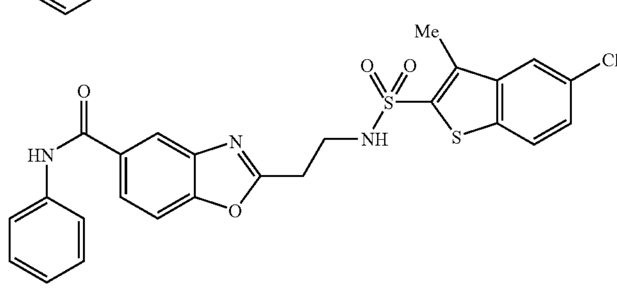 | 2-(2-(5-chloro-3-methylbenzo[b]thiophene-2-sulfonamido)ethyl)-N-phenylbenzo[d]oxazole-5-carboxamide | 3.53 | 526 |

| Example # | Structure | Name | Rt (min) | M + H |
|---|---|---|---|---|
| 15 | 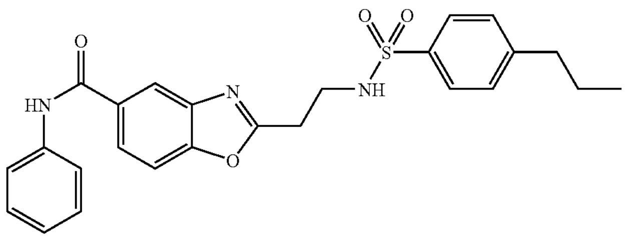 | N-phenyl-2-(2-(4-propylphenylsulfonamido)ethyl)benzo[d]oxazole-5-carboxamide | 3.45 | 464 |
| 16 | 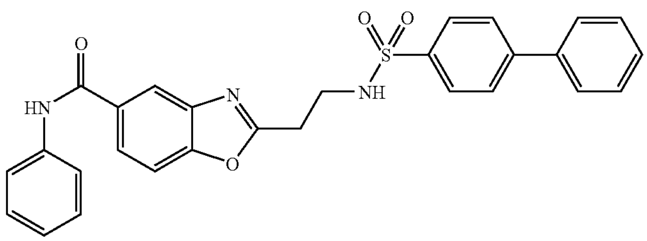 | N-phenyl-2-(2-(4-phenylphenylsulfonamido)ethyl)benzo[d]oxazole-5-carboxamide | 3.44 | 498 |
| 17 | 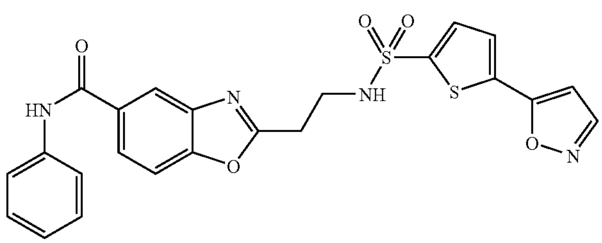 | 2-(2-(2-(isoxazol-5-yl)thiophene-5-sulfonamido)ethyl)-N-phenylbenzo[d]oxazole-5-carboxamide | 2.89 | 495 |
| 18 | 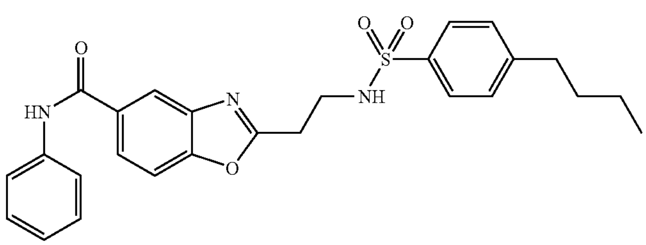 | 2-(2-(4-butylphenylsulfonamido)ethyl)-N-phenylbenzo[d]oxazole-5-carboxamide | 3.62 | 478 |

Example 19

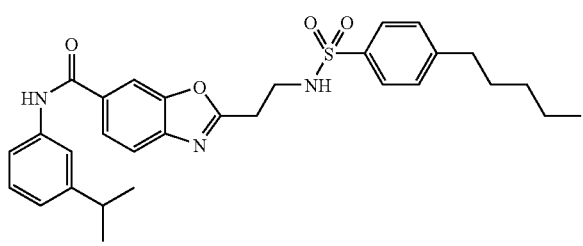

Step 1: 3-(4-pentylphenylsulfonamido)propanoic acid

To a rapidly stirred suspension of the product of Example 1, Step 1 (5.16 g, 18.4 mmol) in water (150 mL) was added sodium peroxide (8.6 mg, 111 mmol). The reaction mixture was heated at 60° C. for 14 h. The reaction was quenched with the addition of 1N aqueous HCl (30 mL) and extracted with ethyl acetate (2×150 mL). The combined organic layers were dried over sodium sulfate and concentrated. The crude intermediate (4.55 g) was used directly in the next step with no further purification. MS m/e 299.

Step 2: 3-hydroxy-4-(3-(4-pentylphenylsulfonamido)propanamido)benzoic acid

To a solution of the product of Step 1 (200 mg, 0.67 mmol) in dry DMF (7 mL) was added 1,1-carbonyldiimidazole (CDI) (120 mg, 0.73 mmol). The resulting mixture was stirred at 40° C. for 1 h, then treated with 3-hydroxy-4-aminobenzoic acid (107 mg, 0.7 mmol). The mixture was stirred at 40° C. for 16 h, then poured into 1N aqueous HCl (100 mL). The resulting yellow precipitate was filtered, washed with diethyl ether, and azeotroped to dryness once from toluene to give the crude title compound (337 mg), which was used directly in the next step without further purification. MS m/e 434.

Step 3:
2-(2-(4-pentylphenylsulfonamido)ethyl)benzo[d]oxazole-6-carboxylic acid

A solution of the product of Step 2 (337 mg, 1.29 mmol) in glacial acetic acid (4 mL) in a sealed tube was heated at 120° C. for 60 h. The solvent was evaporated under reduced pressure, and the resulting residue purified by preparative HPLC to give the product (52 mg). MS m/e 417; HPLC retention time 3.44 min.

Step 4: N-(3-isopropylphenyl)-2-(2-(4-pentylphenylsulfonamido)ethyl)benzo[d]oxazole-6-carboxamide The title compound was prepared from the product of Step 3 in a manner similar to that described for the preparation of the title compound of Example 11 from the product of Example 11, Step 1. MS m/e 534; HPLC retention time 4.19 min.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

A number of references have been cited and the entire disclosures of which are incorporated herein by reference.

What is claimed is:

1. A compound, including all stereoisomers, pharmaceutically acceptable salts, prodrugs and solvates thereof, according to Formula I:

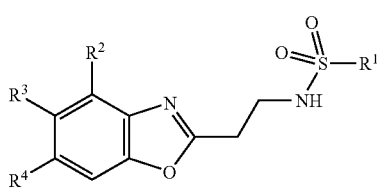

wherein,
$R^1$ is selected from the group consisting of aryl and heteroaryl, wherein the aryl and heteroaryl may optionally be substituted with 0-3 $R^{10}$;
$R^2$ is selected from the group consisting of H and alkyl;
$R^3$ is selected from the group consisting of H, alkyl, nitro and —C(O)N(H)—$R^{10}$;
$R^4$ is selected from the group consisting of H, alkyl and —C(O)N(H)—$R^{10}$, optionally $R^3$ and $R^4$ may be taken together to form a ring;
$R^{10}$ is selected from the group consisting of aryl and heteroaryl, wherein the aryl may optionally be substituted with 0-3 $R^{12}$; and
$R^{12}$ is selected from the group consisting of alkyl and aryl.

2. The compound according to claim 1, wherein $R^1$ is aryl optionally substituted with 0-3 $R^{10}$.

3. The compound according to claim 2, wherein $R^2$ is H.

4. The compound according to claim 3, wherein $R^4$ is H.

5. The compound according to claim 4, wherein $R^3$ is —C(O)N(H)—$R^{10}$.

6. A compound selected from N-(2-Benzooxazol-2-yl-ethyl)-4-pentyl-benzenesulfonamide; Biphenyl-4-sulfonic acid (2-benzooxazol-2-yl-ethyl)-amide; 4-Pentyl-N-[2-(5-phenyl-benzooxazol-2-yl)-ethyl]-benzenesulfonamide; N-[2-(4-Methyl-benzooxazol-2-yl)-ethyl]-4-pentyl-benzenesulfonamide; N-[2-(6-Methyl-benzooxazol-2-yl)-ethyl]-4-pentyl-benzenesulfonamide; N-(2-Naphtho[2,3-d]oxazol-2-yl-ethyl)-4-pentyl-benzenesulfonamide; N-[2-(5-Methyl-benzooxazol-2-yl)-ethyl]-4-pentyl-benzenesulfonamide; N-[2-(5-Nitro-benzooxazol-2-yl)-ethyl]-4-pentyl-benzenesulfonamide; N-[2-(5-sec-Butyl-benzooxazol-2-yl)-ethyl]-4-pentyl-benzenesulfonamide; N-(2-(5-tert-butylbenzo[d]oxazol-2-yl)ethyl)-4-pentylbenzenesulfonamide; N-(3-isopropylphenyl)-2-(2-(4-pentylphenylsulfonamido)ethyl)benzo[d]oxazole-5-carboxamide; 2-(2-(4-pentylphenylsulfonamido)ethyl)-N-phenylbenzo[d]oxazole-5-carboxamide; 2-(2-(4-ethylphenylsulfonamido)ethyl)-N-phenylbenzo[d]oxazole-5-carboxamide; 2-(2-(5-chloro-3-methylbenzo[b]thiophene-2-sulfonamido)ethyl)-N-phenylbenzo[d]oxazole-5-carboxamide; N-phenyl-2-(2-(4-propylphenylsulfonamido)ethyl)benzo[d]oxazole-5-carboxamide; N-phenyl-2-(2-(4-phenylphenylsulfonamido)ethyl)benzo[d]oxazole-5-carboxamide; 2-(2-(2-(isoxazol-5-yl)thiophene-5-sulfonamido)ethyl)-N-phenylbenzo[d]oxazole-5-carboxamide; 2-(2-(4-butylphenylsulfonamido)ethyl)-N-phenylbenzo[d]oxazole-5-carboxamide; and N-(3-isopropylphenyl)-2-(2-(4-pentylphenylsulfonamido)ethyl)benzo[d]oxazole-6-carboxamide.

7. A pharmaceutical composition, comprising:
a compound according to claim 1; and
a pharmaceutically acceptable carrier or diluent.

8. The pharmaceutical composition according to claim 7, further comprising:
at least one additional therapeutic agent.

* * * * *